(12) United States Patent
Zhang et al.

(10) Patent No.: US 12,740,713 B2
(45) Date of Patent: Sep. 22, 2026

(54) SPECTROSCOPIC PHOTOACOUSTIC IMAGING

(71) Applicant: Worcester Polytechnic Institute, Worcester, MA (US)

(72) Inventors: Haichong Zhang, Shrewsbury, MA (US); Shang Gao, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 1068 days.

(21) Appl. No.: 17/869,130

(22) Filed: Jul. 20, 2022

(65) Prior Publication Data

US 2023/0023217 A1 Jan. 26, 2023

Related U.S. Application Data

(60) Provisional application No. 63/223,705, filed on Jul. 20, 2021.

(51) Int. Cl.

| | |
|---|---|
| ***A61B 5/00*** | (2006.01) |
| *A61B 18/00* | (2006.01) |
| *A61B 90/00* | (2016.01) |

(52) U.S. Cl.

CPC .......... *A61B 5/0095* (2013.01); *A61B 5/0036* (2018.08); *A61B 5/0084* (2013.01); (Continued)

(58) Field of Classification Search

CPC ... A61B 5/0095; A61B 5/0036; A61B 5/0084; A61B 2018/00577; A61B 2090/378; (Continued)

(56) References Cited

U.S. PATENT DOCUMENTS

| | | | | |
|---|---|---|---|---|
| 2009/0105588 A1 | 4/2009 | Emelianov et al. | | |
| 2010/0160768 A1* | 6/2010 | Marrouche | ............ A61B 6/503 600/407 | |

(Continued)

FOREIGN PATENT DOCUMENTS

KR 101344951 B1 1/2014

OTHER PUBLICATIONS

Nicholas Dana, B, et al. "In-vitro Photoacoustic Visualization of Myocardial Ablation Lesions", Jan. 2014, pp. 1-17, National Institute of Health.

(Continued)

*Primary Examiner* — Michael J Carey
*Assistant Examiner* — Zainab M Aldarraji
(74) *Attorney, Agent, or Firm* — Armis IP Law, LLC

(57) ABSTRACT

A photoacoustic imaging approach identifies, concurrently with ablation therapy, an extent of the ablation by measuring and rendering a necrotic extent of treated tissue in a treatment region. Laser pulsed light directed at the treatment region induces an acoustic (ultrasound) signal for differentiating ablated tissue from its non-ablative counterpart based on a photoacoustic spectrum variation. The acoustic signal indicates a range of necrotic extent based on a quantified ablated tissue contrast and a total contrast of both necrotic and non-necrotic tissue, defined as a fraction for computing a degree of necrosis. Generation of an image indicating the degree of necrosis allows continuous or near continuous feedback for ablation therapy guidance to ensure complete and effective ablation of the proper tissue in the treatment region.

19 Claims, 6 Drawing Sheets

(52) U.S. Cl.
CPC ............... *A61B 2018/00577* (2013.01); *A61B 2090/378* (2016.02)

(58) Field of Classification Search
CPC ...... A61B 18/1492; A61B 2018/00351; A61B 2018/00446; A61B 2018/0212; A61B 2505/05; A61B 5/0042; A61B 5/0044; A61B 5/4848; A61B 2562/223
See application file for complete search history.

(56) References Cited

U.S. PATENT DOCUMENTS

| | | | | |
|---|---|---|---|---|
| 2012/0310230 | A1 * | 12/2012 | Willis .................... | A61N 1/327<br>606/41 |
| 2013/0102865 | A1 | 4/2013 | Mandelis et al. | |
| 2021/0196229 | A1 | 7/2021 | Boctor et al. | |

OTHER PUBLICATIONS

Gao, Shang, et al, "Cardiac-Gated Spectroscopic Photoacoustic Imaging for Ablation-Induced Necrotic Lesion Visualization: In Vivo Demonstration in a Beating Heart", May 24, 2022, pp. 1-17.
International Search Report, PCT/US2022/037680, Nov. 9, 2022, pp. 1-3.
Iskander-Rizk, Sophinese, et al., "Real-time photoacoustic assessment of radiofrequency ablation lesion formation in the left atrium", Photoacoustics 16 (2019) 100150, pp. 1-10, Published by Elsevier GmbH.
Zhang Haichong K., "Prostate Specific Membrane Antigen (PSMA)—Targeted Photoacoustic Imaging of Prostate Cancer In Vivo", Jun. 17, 2019. pp. 1-11, Published J Biophotonics.

* cited by examiner

SPECTROSCOPIC PHOTOACOUSTIC IMAGING

RELATED APPLICATIONS

This patent application claims the benefit under 35 U.S.C. § 119(e) of U.S. Provisional Patent App. No. 63/223,705, filed Jul. 20, 2021, entitled "SPECTROSCOPIC PHOTOACOUSTIC IMAGING," both incorporated herein by reference in entirety.

STATEMENT OF FEDERALLY SPONSORED RESEARCH AND DEVELOPMENT

This invention was made with government support under grant NIH 10619-GR, awarded by the National Institute for Health (NIH). The government has certain rights in the invention.

BACKGROUND

Ablation therapy provides a minimally invasive process for surgical removal of harmful or extraneous tissue. Several ablation therapies are available, such as radiofrequency (RF) ablation, cryoablation, and pulsed-field ablation (PFA), which generally provided targeted elimination of tissue by rendering the tissue in a necrotic state. Cardiac and neurological approaches are beneficial, as the precision of ablation allows tissue regions associated with or contributing to harmful or erratic neurological signals to be eliminated without disrupting the important neurological or cardiac system function.

SUMMARY

A photoacoustic imaging approach identifies, concurrently with ablation therapy, an extent of the ablation by measuring and rendering a necrotic extent of treated tissue in a treatment region. Laser pulsed light directed at the treatment region induces an acoustic (ultrasound) signal for differentiating ablated tissue from its non-ablative counterpart based on a photoacoustic spectrum variation. The acoustic signal indicates a range of necrotic extent based on a quantified ablated tissue contrast and a total contrast of both necrotic and non-necrotic tissue, defined as a fraction for computing a degree of necrosis. Generation of an image indicating the degree of necrosis allows continuous or near continuous feedback for ablation therapy guidance to ensure complete and effective ablation of the proper tissue in the treatment region.

Configurations herein are based, in part, on the observation that conventional ablation therapies effectively remove problematic tissue regions, particularly in cardiac and neurological areas where tissue manipulation demands precise accuracy and control. Unfortunately, conventional approaches to ablation therapy suffer from the shortcoming of incomplete ablation due to a lack of concurrency in the ablation administration and validation of the treated area. Conventional approaches rely on either CT (Computed Tomography) or MRI (Magnetic Resonance Imaging) to evaluate ablation necrotic extent (NE), which are limited by the inability to provide real-time (RT) feedback of the ablation process. Ablation can be effective in treatment of cardiac Atrial Fibrillation (AF), however cardiac AF recurrence following catheter ablation therapy results from electrical recovery of ablated myocardial tissues over time that creates gaps of conductive tissues within the previously ablated tissue. Neurological approaches, similarly, target neurological tissue contributing to erratic electrical characteristics affecting neurological impulses.

A major limitation of the current catheter ablation therapy is the lack of technology to distinguish between reversible (e.g., tissue edema) and irreversible lesions (e.g. tissue necrosis) during the procedure. An intraoperative technology to evaluate ablation lesions would significantly decrease the recurrence rate. While cardiac magnetic resonance (CMR) can visualize acute and chronic ablation lesions, it is not accessible intraoperatively in most institutions and thus cannot provide the operator with actionable information during the procedure. While intracardiac echocardiography (ICE) is widely used during ablation procedures by offering visualization of anatomical landmarks, characterization of the tissue substrate is limited. Therefore, there is an unmet clinical need for a noninvasive intraoperative imaging system to differentiate between the necrotic and viable tissues to improve the outcomes of ablation therapy.

Conventional approaches, therefore, suffer from the shortcoming of an effective, timely feedback for accessing completeness and extent of necrotic tissue resulting from ablation treatment. Accordingly, configurations herein substantially overcome the shortcoming of conventional approaches by providing spectroscopic photoacoustic imaging of a tissue treatment region for rendering a necrotic extent indicative of a degree of necrosis, not just necrotic existence, of the tissue. A generated image mapping the ablation-treated region provides a coloration indicating a range of necrotic extent of the affected tissues, concurrently with the ablation therapy, to allow complete, non-excessive ablation to be accurately administered.

Photoacoustic (PA) imaging is an emerging imaging modality based on laser-generated ultrasound, depicting tissue optical absorption. Different materials possess unique spectroscopic characteristics and those can be used to characterize different types of chromophores. The imaging modality has been widely used for vascular mapping, tumor detection, and oxygenation mapping. The implementation of PA imaging has been investigated in intravascular imaging for vulnerable plaques detection, as well as the intraplaque hemorrhages in carotid artery plaque.

In further detail, configurations herein present a system, method and apparatus of spectroscopic photoacoustic imaging and treatment of an afflicted region, including directing a photonic signal at a tissue treatment site, and receiving a photoacoustic signal indicative of a temperature induced response of the tissue resulting from the photonic signal. The photonic signal is a pulsed laser that induces a rapid thermal expansion which generates the photoacoustic waves, which are then received and used for rendering a necrotic extent indicative of a degree of necrosis of the tissue. Rendering logic determines the necrotic extent based on a contrast of spectral decomposition between the necrotic and non-necrotic tissue in the received acoustic signal.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
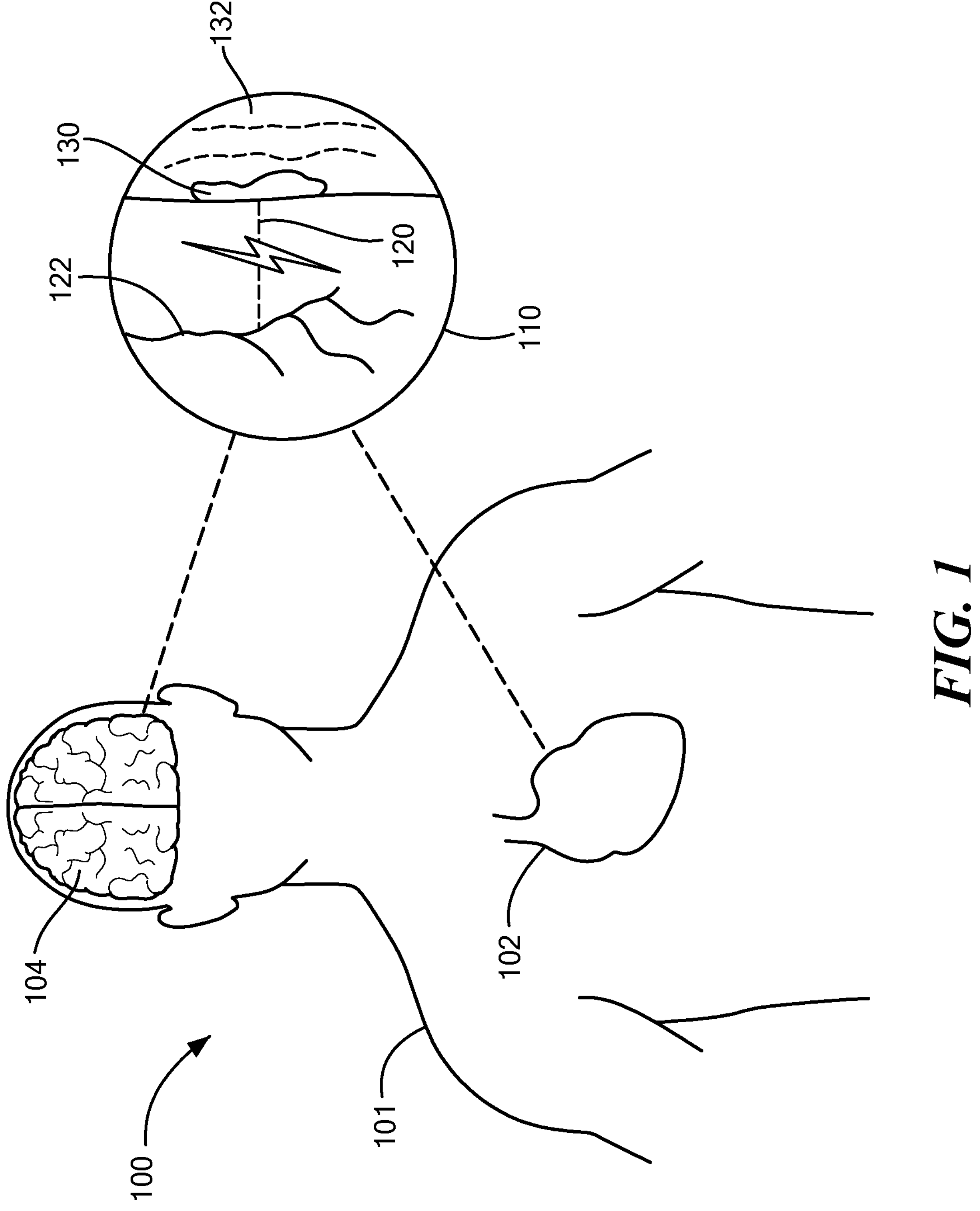
FIG. 1 is a system context diagram of a medical diagnosis environment suitable for use with configurations herein.

The description below presents an example of an imaging apparatus and system employing spectroscopic photoacoustic (PA) imaging for visualization of ablation-induced necrotic lesions to provide image-based monitoring of necrotic extent of the tissue during the ablation procedure. A method of spectroscopic photoacoustic imaging of a tissue treatment region includes imaging a tissue region for distinguishing necrotic and viable tissue, and rendering a mapping for providing a degree of necrosis for necrotic tissue. The rendered mapping provides a range or degree of necrosis, rather than a binary threshold mapping, to illustrate not only necrotic regions but also a degree of necrosis.

Therapeutic measures deliver ablation therapy to portions of the tissue region based on the rendered mapping. Imaging further includes directing a multiwavelength photoacoustic signal at the tissue region, such that the multiwavelength photoacoustic signal provides specific target contrasts based on spectral decomposition of the necrotic and viable (non-necrotic) tissue. From the PA signal, a necrotic extent (NE) is computed based on a contribution from the necrotic tissue contrast with respect to the total contrast combining with that of non-necrotic tissue, allowing computation of a continuous NE colormap of the tissue region.

The disclosed approach is configurable with ablation therapy including percutaneous catheter ablation therapy such as radiofrequency (RF) ablation, cryoablation, and pulsed-field ablation (PFA). Further, while any suitable tissue region may be employed, the PA approach is particularly suited for myocardial tissues and neurological tissue. Other uses include procedures on the liver, kidney, and lung tissues, which also often involve ablation therapy.

Radiofrequency (RF) catheter ablation is an effective therapy for a wide-range cardiac arrhythmia. However, the current RF systems lack direct, intra-operative, real-time feedback on ablation lesion formation, making assessment difficult. Cardiac magnetic resonance (CMR) can provide some degree of visualization of ablation lesions, but its intra-operative usage continues to be refined. A portable, intra-operative imaging system to visualize the growth of the ablation necrotic region can provide real-time feedback to the operator, doctor or medical technician, and thus is expected to reduce arrhythmia recurrence and procedural complications by avoiding incomplete and excessive ablation, respectively. Photoacoustic (PA) imaging is a biomedical imaging modality based on laser-generated ultrasound. Previous research showed that the PA spectrum of the non-ablated tissue has a prominent hump near 760 nm leaning towards the hemoglobin spectrum and is absent in that of the ablated tissue. Based on these underpinnings, configurations herein disclose a PA image-guided ablation system with a side-firing linear array transducer that enables intraoperative necrotic region visualization. The spectroscopic decomposition process is applicable to identify lesions based on spectrum differences.

FIG. 1 is a system context diagram of a medical diagnosis environment suitable for use with configurations herein. Referring to FIG. 1, in a medical treatment environment 100, a tissue treatment region 110 may pertain to cardiac (heart) regions 102 or neurological/central nervous system (CNS) regions 104 of a patient 101. In the tissue treatment region 110, erratic electrical signals 120 may travel through bodily organs or tissue from neurons 122 or other biochemical effect. Ablation therapy may be invoked for eliminating certain electrical pathways conducting these signals by forming an ablation region 130 of necrotic tissue between a source or neuron 122 emanating the signal and a receiving or destination tissue 132 adversely affected. Organs such as the heart and brain operate on complex and precise transport of electrical signals, and improper or erratic signals 120 can be detrimental or fatal. Visualization of the ablation region 130 as defined herein ensures that the ablation is complete, such that the tissue does not subsequently heal and resume conductivity of the erratic signals, and that the ablation region 130 does not extend any further than called for by the medical diagnosis, lest excessive elimination of healthy tissue occurs.

Figure 2:
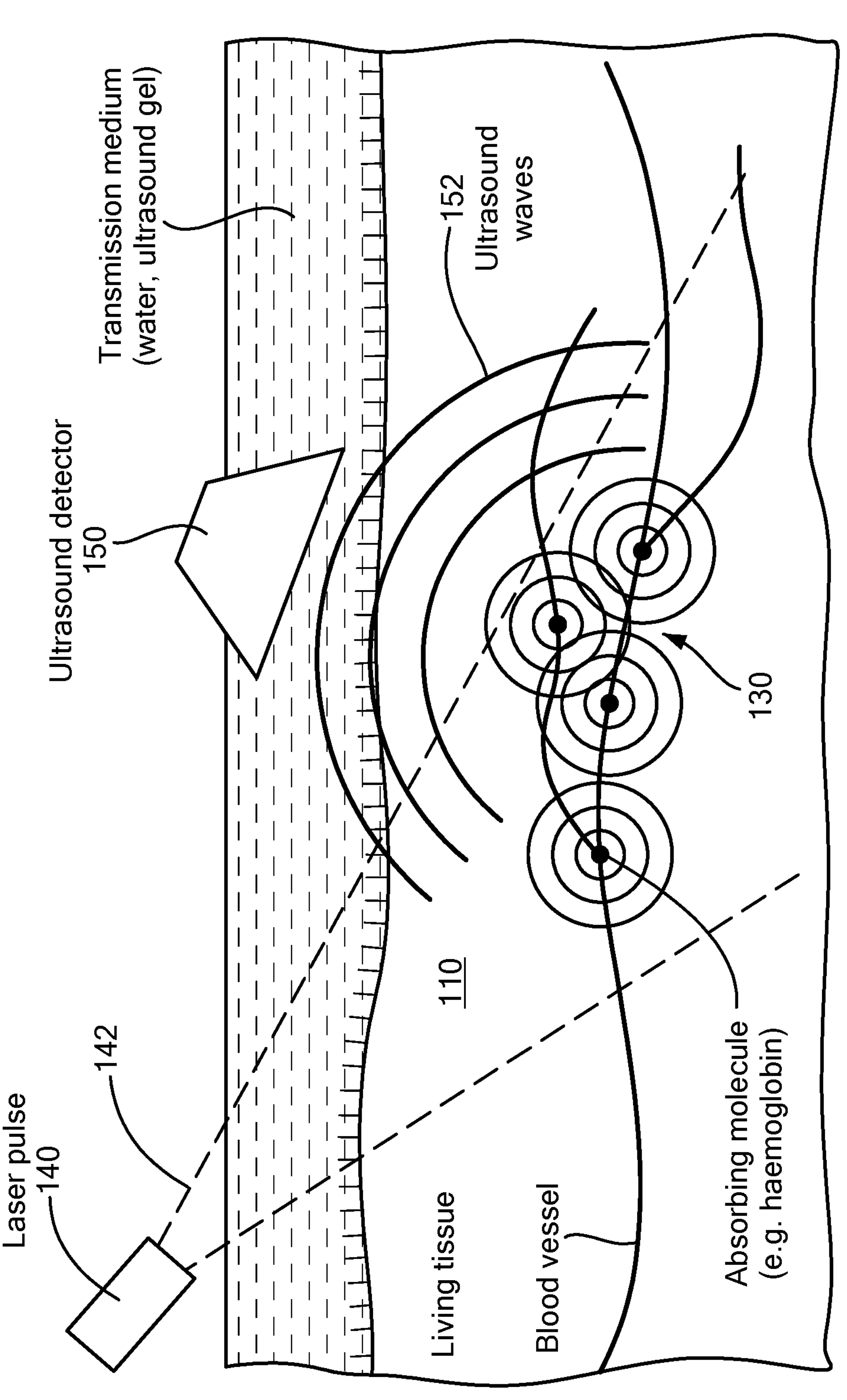
FIG. 2 is a schematic diagram of the disclosed approach in the environment of FIG. 1.

FIG. 2 is a schematic diagram of the disclosed approach in the environment of FIG. 1. Referring to FIGS. 1 and 2, the method of spectroscopic photoacoustic imaging of a tissue treatment region 110 includes directing a photonic signal 142 at the tissue treatment region 110 from a light source 140, and receiving an acoustic signal 152 indicative of a temperature induced response of the tissue resulting from the photonic signal. An ultrasound (US) detector 150, such as an US transducer or array of transducers, receives the acoustic (photoacoustic) signals 152 for rendering a necrotic extent indicative of a degree of necrosis of the tissue.

A spectroscopic photoacoustic (PA) imaging device provides for the visualization of ablation-induced necrotic lesions during the ablation procedure. The real-time feedback is used by the operator to monitor and control the amount and quality of ablation. The measured PA signals are modeled as the combination of multiple absorber contrasts. The specific target contrasts can be recovered through "spectral decomposition"/"spectral unmixing" from the measured multiwavelength PA spectrum, assuming each contrast source has unique PA spectrum. The PA spectrum of the ablation-induced necrotic tissues is known to be different from that of viable myocardium. Thus, spectral decomposition can distinguish contrasts between necrotic and viable tissues. To visualize the necrotic lesions, direct mapping of decomposed ablated tissue contrast and binary thresholding of decomposed contrasts are reported.

The PA response induces a contrast in the acoustic signal 152, meaning a measurable and quantifiable value indicative of:

1) The strength of the signal response (e.g. the photoacoustic response generated by the laser pulse); and
2) The difference of the signal response (e.g. photoacoustic response or decomposed target signal specific response) with respect to the response from the neighboring area.

Such a contrast refers to the ultrasonic imaging medium, and need not employ a contrasting pigmentation, dye or radioactive substance. In the context herein, the ablated tissue has a quantifiable contrast compared to the non-ablated counterpart, which may be expressed as a photoacoustic response difference compared to different (necrotic/non-necrotic) tissue types.

While conventional approaches depict the presence of necrotic tissue, the clinical practice requires observing the lesion boundary between viable myocardium and detecting the presence of ablation "gaps" for assessing insufficient ablation. Such information is hard to assess by conventional visualization methods because the decomposed contrast reliability is subject to the illuminated fluence homogeneity, which is hardly satisfied in vivo. The thresholding approach requires manual interpretation. Approaches herein realize a need to map not only the necrotic contrast alone but the relationship of the necrotic and non-necrotic contrasts. Disclosed approaches introduce a new necrotic region mapping method, quantifying the extent of ablation-induced necrosis with respect to the non-necrotic viable tissue. After decomposing the contrast of two myocardium states, the necrotic extent (NE) is quantified based on the contribution from the necrotic tissue contrast with respect to the total contrast combining with that of non-necrotic tissue. The NE map is presented through a continuous colormap, and rendered on a visual device for concurrent observation.

Biomedical materials each have unique optical absorption characteristics consisting of PA spectra. The measured PA signals are consisted by the combination of contrasts from multiple chromophores and contrast agents. Decomposing each material contribution and forming a spectroscopic photoacoustic (sPA) image can be conducted through spectroscopic decomposition (also known as material decomposition or spectral unmixing). Such a technology has been well explored in blood oxygenation mapping and contrast agent enhanced imaging. Based on the assumption that the received PA spectrum consists of a linear combination of multiple chromophores, the contribution from each contrast is estimated as $$\underset{m_{1,2,\ldots,M}}{\text{Argmin}}\left\|\sum_{W}\left(p-\sum_{i=1}^{M}m_i\mu_{a,i}\right)^2\right\|$$

where p is the measured PA spectrum, i is the contrast source number, M is the number of absorbers, μa is the absorption spectrum of contrast i, and W presents the wavelengths used.

Figures 3, 4:
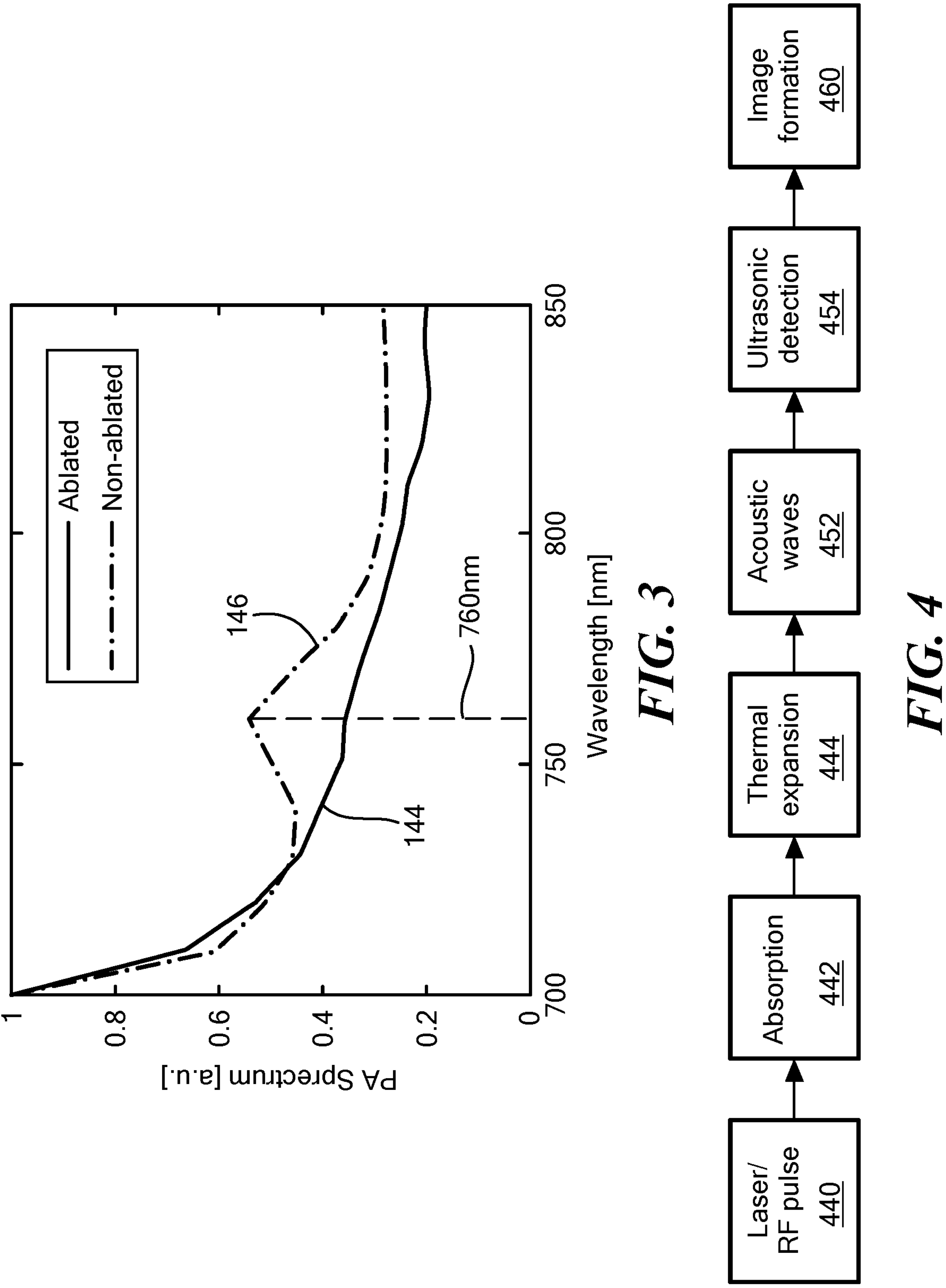
FIG. 3 is a graph of wavelengths of the photoacoustic signal of FIGS. 1 and 2.
FIG. 4 is a flow diagram of an example of the approach of FIGS. 1-3.

FIG. 3 is a graph of wavelengths of the photoacoustic signal of FIGS. 1 and 2. Referring to FIG. 3, spectroscopic decomposition distinguishes the contribution of the contrast of the ablated tissue 144 from that of the non-ablated tissue 146. With the reference PA spectra from ablated and non-ablated tissues as the input, the contrast contribution from two tissue types is decomposed. The photonic signal 142 is expected to be a laser signal having a wavelength based on a response of hemoglobin or Tin the tissue. FIG. 3 shows the PA spectra used, and shows that the spectrum of the non-ablated tissue 146 has a prominent hump near 760 nm leaning towards the hemoglobin spectrum and is absent in that of the ablated tissue 144.

The second step of quantifying the extent of tissue necrosis is to estimate the contribution of the ablated tissue contrast with respect to the combination with the non-ablated tissue contrast based on the decomposed contrast from both ablated and non-ablated tissue types. This is based on the assumption that non-necrotic tissue should not contain the contrast from the ablated tissue and fully ablated necrotic tissue should not contain that from the non-ablated tissue. The necrotic extent (NE) metric presents the intensity ratio between ablated tissue contrast (mAb) and the summation of ablated tissue contrast with non-ablated tissue (mN−Ab), as shown:

$$NE=\frac{m_{Ab}}{m_{Ab}+m_{N-Ab}}$$

Computational logic computes the necrotic extent based on a contrast of spectral decomposition between the necrotic and non-necrotic tissue in the received acoustic signal. Such a mapping method is capable of capturing the transition between two tissue statuses.

In addition, it is required to account for the potential occurrence of insufficient light illumination during scanning and the presence of background noise. In such case, the measured PA spectrum will contain signals non-specific to neither ablated nor non-ablated tissue spectra, which could affect the estimation accuracy of both ablated and non-ablated tissue contrasts. Therefore, we regard those non-specific signal spectra as residual and filter out the pixel containing high residual contrast with respect to the total PA contrast to only visualize the contrast with higher confidence in NE mapping, as:

$$\frac{\sum_{W}\left(p-\sum_{i=1}^{M}m_i\mu_{a,i}\right)}{\sum_{W}p}<R_{thres}$$

where $R_{thres}$ is the residual threshold value which is set at 0.2. This threshold enhances the tissue contrast in the scanned image by differentiating the low-intensity PA signal generated by the tissue from noise signals. Parameter tuning may alter this threshold. The output NE map is displayed with a continuous colormap to show the transition of tissue necrosis in an intuitive visual sense, in which mapped colors indicate ablated and non-ablated tissues, respectively. A NE value of 0.2 was set for defining the boundary of the ablated region, however this parameter may be tuned as treatment demands.

FIG. 4 is a flow diagram of an example of the approach of FIGS. 1-3. Referring to FIGS. 1-4, at step 440, the light source 140 generates a photonic signal 142 of a pulsed laser light. In the example configuration, the light source is a suitable laser source for producing the response of FIG. 3, and includes selection of a wavelength of the laser light based on a prominence of a photoacoustic response in the returned acoustic signal corresponding to hemoglobin. Hemoglobin, and alternatively myoglobin, are prevalent only in living, non-necrotic tissue, resulting in the different contrasts from necrotic and non-necrotic tissue. The light source 140 pulses the laser light for inducing the photoacoustic response in the tissue 110 based on heating and expansion of the cells in the tissue resulting in the photoacoustic response. This may be loosely likened to a thunder clap, where the electrical activity, or "bolt" of lightning induces rapid expansion of air resulting in the thunder "clap."

Absorption of the laser occurs at step 442, where spectral decomposition is based on optical absorption characteristics between necrotic and non-necrotic tissue resulting from chromophores in the tissue. Absorption results in heating and thermal expansion (step 444), according to a pattern based on the laser pulse, which generates the acoustic signal (waves), as shown at step 452.

The ultrasound detector 150 or detectors receives the acoustic signal 152, as shown at step 454, indicative of the necrotic and non-necrotic state of the tissue. Each of an occurrence or iteration of the acoustic signal 152 represents a particular region of the tissue in the treatment region 110. Successive iterations over different positions in the tissue treatment region 110 each define different portions or pixels of the ablation region 130, and/or portions of necrotic and non-necrotic tissue. Mapping of the received acoustic signal to a visual rendering of an image quantifies the extent of ablation-induced necrosis with respect to the non-necrotic viable tissue, as depicted at step 460.

Figure 5:
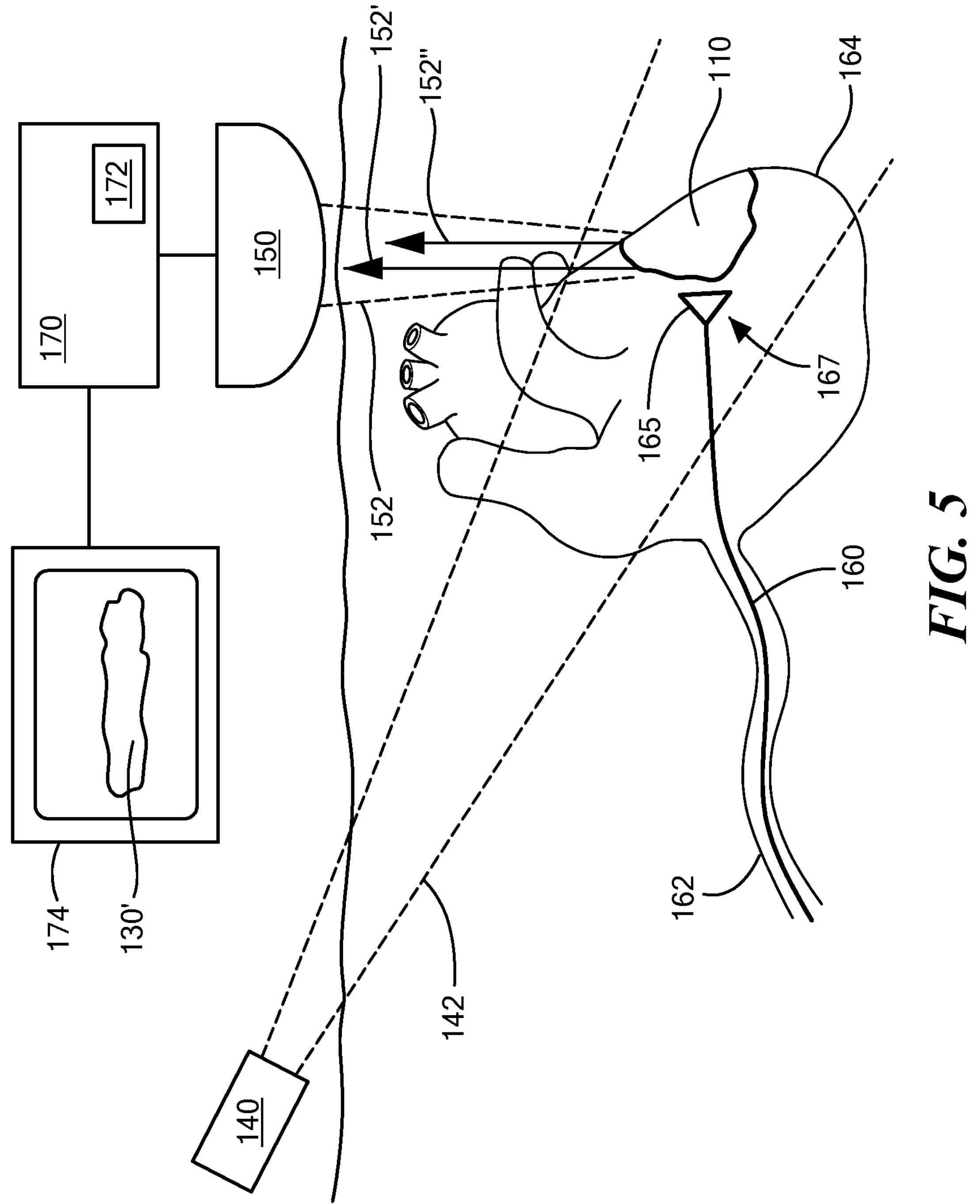
FIG. 5 shows device usage according to the approach of FIGS. 1-4.

FIG. 5 shows device usage according to the approach of FIGS. 1-4. Any suitable tissue may be employed for a PA response as disclosed herein, however cardiac and neurological approaches are particularly amenable. Referring to FIGS. 1-5, imaging includes directing an ablation instrument to the tissue region 110, typically based on an indication of electrical anomalies in the tissue region. These electrical anomalies are often the cause of ailments such as atrial fibrillation and neurological disorders.

In the example of FIG. 5, a catheter 160 having an ablation end 170 advances along a blood vessel 162 to the heart 164 for accessing the treatment tissue region 110. The ablation end 167 may include any suitable ablation mechanism 165, such as RF or cryogenic, and is invoked to apply an ablation therapy to the tissue region 110 for mitigating the electrical anomalies. As indicated above, the light source 140 and ultrasound detector 150 operate concurrently or alternately in short succession for receiving acoustic signals 152 corresponding to both ablated 152' and non-ablated 152" tissue. The light source is typically within several centimeters of the imaged region, and may be external or surgically disposed internally, such as with or adjacent to a catheter. A processing device 170 invokes computational logic 172 for computing the necrotic extend and producing a rendered image 130' of the necrotic region on a rendering device 174. The processing device 170 performs a spectroscopic decomposition to distinguish a contribution of a contrast of the ablated tissue from that of the non-ablated tissue. This includes identifying, in the spectral decomposition, a contrast contribution in the received acoustic signal resulting from hemoglobin or myoglobin indicative of non-necrotic tissue. Feedback based on the necrotic extent allows selective adjustment of an intensity of the ablation therapy at the ablation end 167 based on the necrotic extent.

Figure 6:
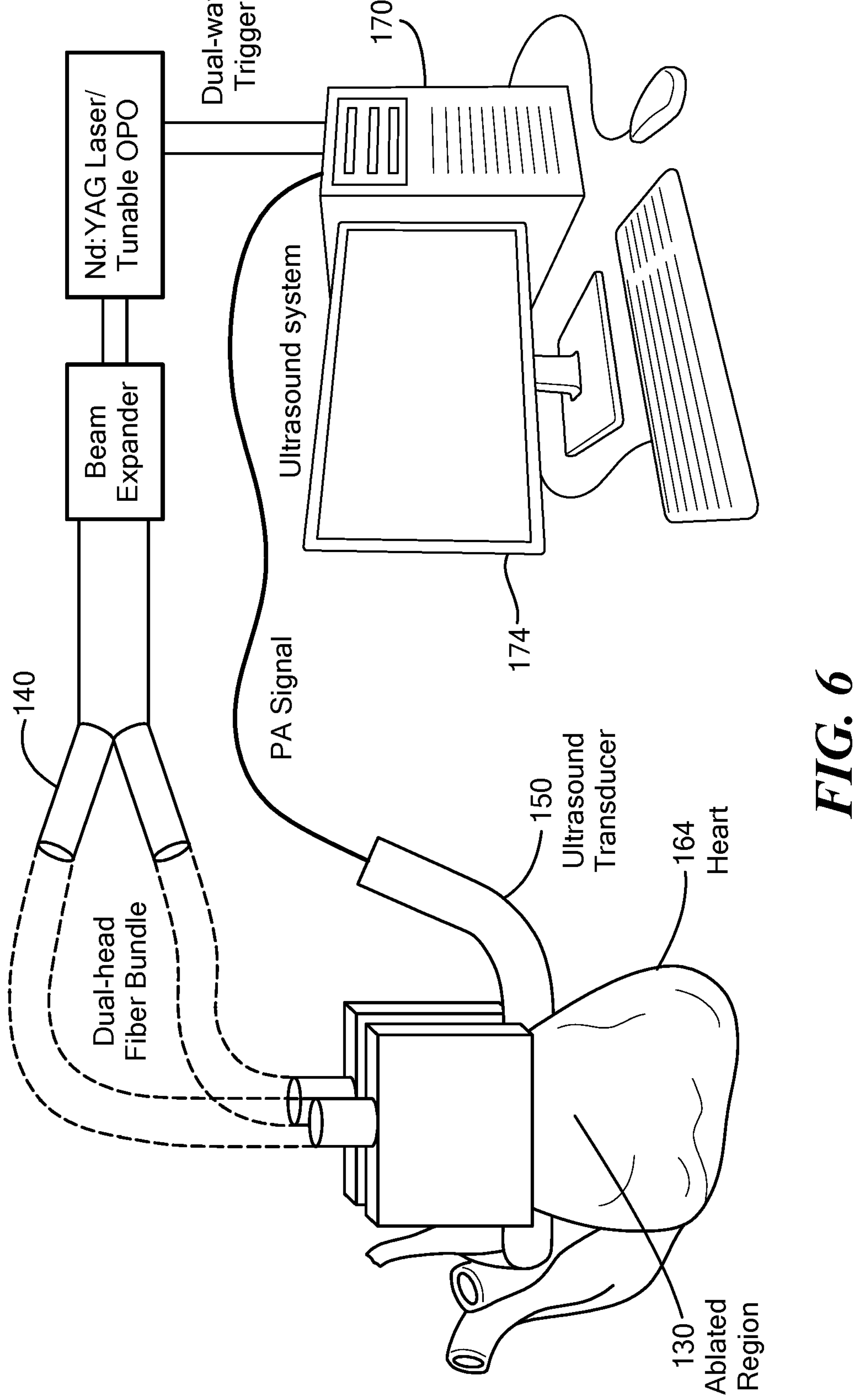
FIG. 6 is an apparatus suitable for use with image rendering using the approach of FIGS. 1-5.

A complete system for medical ablation with photoacoustic imaging therefore includes the ablation device or probe with an ablation end 167, laser light source 150, and ultrasound detector 150 or probe. FIG. 6 is an apparatus suitable for use with image rendering using the approach of FIGS. 1-5. Referring to FIGS. 1-6, an example PA imaging system setup used is shown in FIG. 6. A 128 elements linear-array ultrasound (US) transducer probe (Philips ATL Lap L9-5, Philips, Netherlands) was used as the ultrasound detector 150. The Verasonics Vantage system (Vantage 256, Verasonics, USA) was used as the data acquisition device. A Q-switched Nd:YAG laser light source 140 (Q-smart 450, Quantel, USA) with an optical parametric oscillator (OPO) (MagicPRISM, OPOTEK, USA) was used, which is capable of generating a laser pulse at the wavelength range of 690-950 nm at a repetition rate of 20 Hz with 5 ns pulse duration. The disclosed setup is exemplary; any suitable configuration for generating and analyzing the PA signals as described above may be employed.

A particular usage concerns real time feedback and image reconstruction of the necrotic region 130 (and adjacent non-necrotic regions). This is best rendered by a colored mapping with different colors depicting the necrotic extent, and allows rendering of the necrotic region image 130' concurrently with ablation therapy. Real-time visual feedback on the necrotic region growth is expected to reduce recurrence and procedural complications by avoiding incomplete and excessive ablation, respectively. To demonstrate the real-time imaging feasibility, a particular configuration performs continuous PA recording on an ex vivo tissue during Radio Frequency Ablation (RFA). Three wavelengths (700, 740, and 760 nm) covering the PA spectral difference between necrotic and viable tissues were used. The growth of the necrotic lesion area could be visualized through spectral decomposition and NE mapping. Direct comparisons between the acquired image and gross pathology suggested that our early prototype could well capture necrotic lesion size. The measured necrotic lesion was 5.93 mm in width, matching with the actual width of 6.2 mm. The temporal change of the necrotic region width captures the ablation progression over time. Other suitable device configurations may be employed. In a cardiac treatment regime, an expected configuration includes integrating the ablation instrument with a catheter configured for intravenous displacement along a blood vessel. Usage includes accessing the tissue region adjacent to the blood vessel. Another implementation includes integrating the ablation instrument with an elongated probe configured for insertion into neurological tissue, and accessing the tissue region via proximity of the elongated probe.

A dictionary-based spectral decomposition can be employed to enhance the sensitivity and specificity of quantifying necrotic and viable myocardium contrasts. Conventional spectral decomposition utilizes an experimentally obtained single representative PA spectrum for each myocardium state. However, a single spectrum per state does not reflect the variable PA spectra under complex tissue characteristics, compromising the estimation accuracy. The variable PA spectra of myocardium consist of hemichrome, metmyoglobin, and protein denaturalization contents. The composition of those contents could vary at different heart regions and subjects. Reversible myocardium, known as edema, has unique tissue characteristics. The perfusion-induced tissue oxygenation may affect the absorbance of Hb and myoglobin. Those variations are not considered in the conventional spectral decomposition, resulting in incorrect estimation. The proposed method utilizes a large set of synthesized PA spectra to quantify contrasts from necrotic and viable myocardium with variable PA spectra. To create the PA spectra dictionary, the PA spectra from multiple regions of multiple ex vivo swine myocardium samples before and after applying ablation. To incorporate blood perfusion-induced tissue oxygenation variation, the fractional combinations of hemoglobin and myoglobin spectrum at different oxygenation levels will be added for each obtained PA spectrum. The dictionary-based spectral decomposition can be formulated as:

$$\underset{c_{Ab,1,2,\ldots,N},c_{N-Ab,1,2,\ldots,N}}{\operatorname{argmin}} \left\| \sum_{\lambda}^{A} \left( p_\lambda - \sum_{n}^{N} d_n ( c_{Ab,n} s_{Ab,\lambda,n} + c_{N-Ab,n} s_{N-Ab,\lambda,n} ) \right) \right\| \text{ s.t. } \sum_{n}^{N} d_n = 1, \quad (1)$$

-continued $$c'_{Ab} = :\sum_{n}^{N} c_{Ab,n},\ c'_{N-Ab} = \sum_{n}^{N} c_{N-Ab,n} \tag{2}$$

where $d_n$ presents the contribution from the spectrum number n. The total number of PA spectra is N. $s_{Ab,n}$ and $s_{N-Ab,n}$ are a particular spectra with n for two states.

FIG. 6 is a flow diagram of image construction for necrotic extent rendering as in FIGS. 1-5. The imaging speed of sPA imaging is determined by factors such as the laser pulse repetition frequency (typically 10-20 Hz or at most 100 Hz) and the number of wavelengths used for spectroscopic decomposition. Additionally, the signal-to-noise ratio (SNR) of the PA signals in the in vivo environment is expected to be compromised due to the limited space for placing light delivery fibers and light absorption from blood, requiring frame averaging to enhance the SNR. Hence, a certain temporal duration of PA data is required for sPA imaging in an intracardiac environment. However, continuous drastic tissue motion due to heartbeat introduces severe motion artifacts and prevents direct data processing, motivating us to introduce cardiac gating to enable in vivo sPA imaging of a beating heart. Specifically, we track and map the recorded PA data to a specific time point with respect to a cardiac cycle. The image similarity with respect to the specific time point is used to sort and align PA data, in which averaging filter and spectral decomposition, and necrotic extent mapping are applied.

To track the temporal variation and similarly of PA images over time, the approach computes the 2D cross-correlation coefficient of two PA image frames. The coefficient, R, is defined as a scalar value between 0 and 1, of which 1 suggests two input images are identical, and 0 indicates the opposite. The variable m, n is the pixel number in the input 2D envelope detected PA images A and B, and A and B represent the mean value of A and B intensity.

$$R = \frac{\sum_m \sum_n (A_{mn} - \overline{A})(B_{mn} - \overline{B})}{\sqrt{\left(\sum_m \sum_n (A_{mn} - \overline{A})^2\right)\left(\sum_m \sum_n (B_{mn} - \overline{B})^2\right)}}$$

Based on the similarity between any two PA imaging frames, a high cross-correlation coefficient indicates the two cardiac PA images were taken when the cardiac tissue appears at a similar location in the field of view (FOV). Yet, the high coefficient, R, alone is not sufficient to extract a cardiac cycle because the tissue surface passes a similar location in the imaging FOV twice in a cardiac cycle during the contraction and relaxation. The contraction and relaxation data should be distinguished because the muscle status of the cardiac tissue could be different between them. This could introduce additional noise in the spectrum when images were averaged. Therefore, we categorized the PA frames that based on not only the image similarity but also the isolation between the contraction and relaxation phases in a cardiac cycle.

To examine the similarity alignment of two frames with respect to a cardiac cycle, we computed the image correlation coefficient in the temporal axis. The temporal correlation coefficient was defined as RT shown below, where R is the correlation coefficient defined below evaluates the similarity of PA image frame f with respect to a reference frame $f^r$. The correlation coefficient of the frame i was compared, as well as the frames (i−j) in the previous cardiac cycle with the length of M image frame. The sorted high RT frames guarantee both similarities in tissue position in the image FOV and the alignment with respect to a cardiac cycle.

$$R_T = \frac{\sum_j^M R(f_{i-j}, f_{i-j}^r)}{M}$$

The aligned PA images at the same timing in a cardiac cycle were averaged to offer SNR-improved cardiac gated (CG) PA images.

Figure 7:
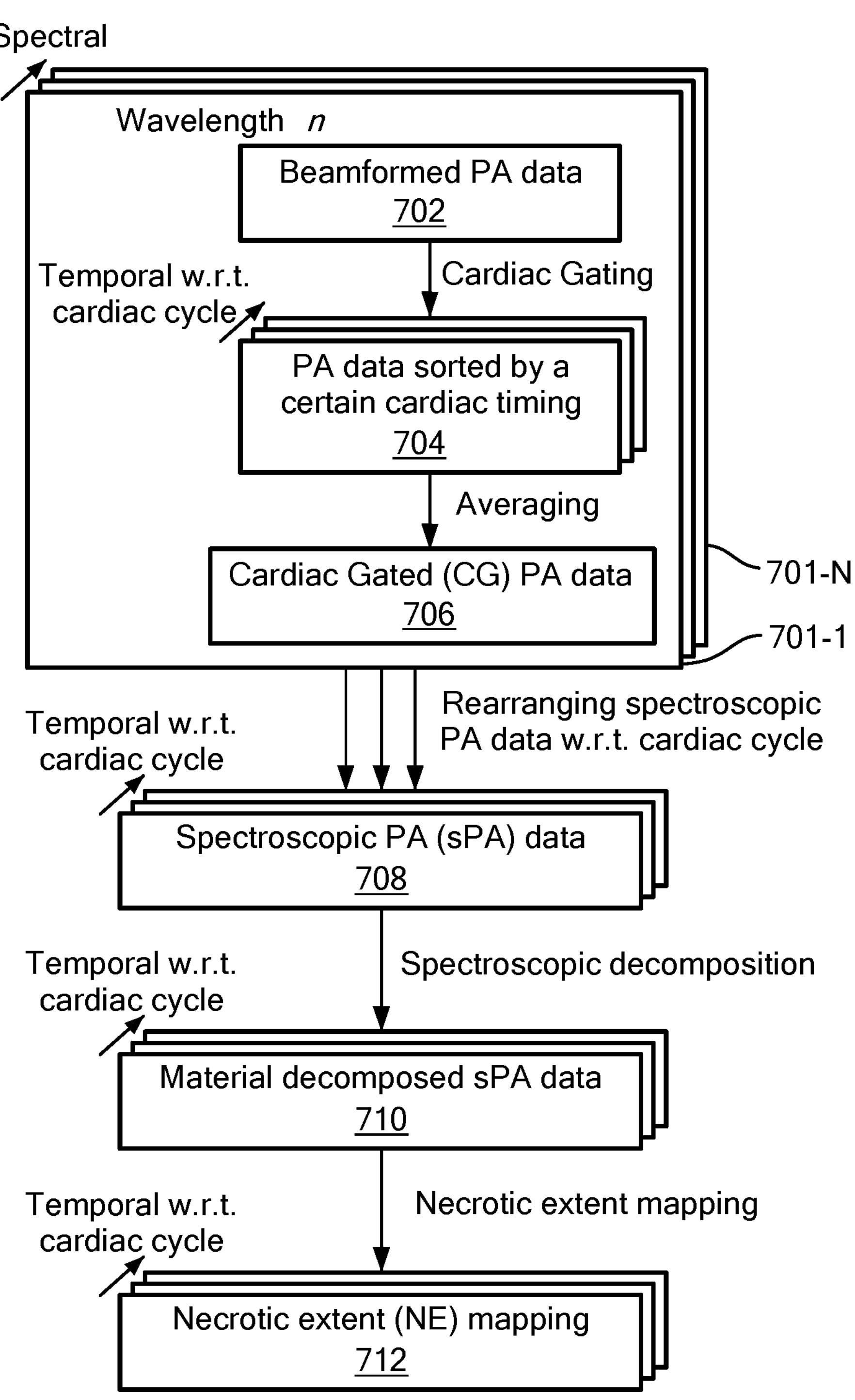
FIG. 7 is a flow diagram of image construction for necrotic extent rendering using the apparatus of FIG. 6.

FIG. 7 summarizes the workflow of signal processing for the recorded PA images with the proposed CG-sPA imaging incorporating both cardiac gating and spectroscopic decomposition. At step 702, the acquired PA channel data were first beamformed by Delay-and-Sum (DAS) algorithm and envelope detected and then sorted based on their PA excitation wavelengths 701-1 . . . 701-N. In each sorted wavelength frame set, a routine of the cardiac tissue surface motion was observed and it was tracked with RT to a defined reference frame in a particular cardiac cycle, as depicted at step 704, At each stage of the CG, the RT of all the recorded PA frames was calculated with respect to the reference frame at this cardiac cycle, shown at step 706. Frames with calculated RT above the threshold (defined as 0.4 in the example) were selected and averaged, as depicted at step 708. The same process was applied to all individual illuminated wavelength data. The SNR enhanced outputs through averaging at each wavelength were combined as a CG sPA data set for the following spectroscopic decomposition to distinguish ablated and non-ablated tissue spectrums, as depicted at step 710, The NE map was computed as described above, at step 712. The process was then repeated to the frames throughout a cardiac cycle.

Those skilled in the art should readily appreciate that the programs and methods defined herein are deliverable to a user processing and rendering device in many forms, including but not limited to a) information permanently stored on non-writeable storage media such as ROM devices, b) information alterably stored on writeable non-transitory storage media such as solid state drives (SSDs) and media, flash drives, floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions, including virtual machines and hypervisor controlled execution environments. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method of spectroscopic photoacoustic imaging of a tissue treatment region, comprising:

directing a photonic signal at a tissue treatment site;

receiving an acoustic signal indicative of a temperature induced response of the tissue resulting from the photonic signal;

computing a necrotic extent based on a fraction of quantified ablated tissue contrast over a total contrast from both ablated and non-ablated tissues based on a ratio attributable to respective different wavelengths corresponding to the necrotic and non-necrotic tissue, and visualizing the computed necrotic extent as a continuous colormap to highlight the necrotic tissue and extent; and rendering the necrotic extent indicative of a degree of necrosis of the tissue by mapping the received acoustic signal to a visual rendering for quantifying the extent of ablation-induced necrosis with respect to a non-necrotic viable tissue.

2. The method of claim 1 further comprising determining the necrotic extent based on a contrast of spectral decomposition between a necrotic tissue and the non-necrotic tissue viable in the received acoustic signal.

3. The method of claim 2 wherein the spectral decomposition is based on optical absorption characteristics between necrotic and non-necrotic tissue resulting from chromophores in the tissue.

4. The method of claim 2 further comprising performing spectroscopic decomposition to distinguish a contribution of a contrast of the ablated tissue from that of a non-ablated tissue.

5. The method of claim 2 further comprising identifying, in the spectral decomposition, a contrast contribution in the received acoustic signal resulting from hemoglobin or myoglobin indicative of non-necrotic tissue.

6. The method of claim 1 further comprising:

selecting a wavelength of a laser light defining the photonic signal based on a prominence of a photoacoustic response in the returned acoustic signal corresponding to hemoglobin; and pulsing the laser light for inducing the photoacoustic response in the tissue based on heating and expansion of the cells in the tissue resulting in the photoacoustic response.

7. The method of claim 1 further comprising:

directing an ablation instrument to the tissue region based on an indication of electrical anomalies in the tissue region;

applying an ablation therapy to the tissue region for mitigating the electrical anomalies; and selectively adjusting an intensity of the ablation therapy based on the necrotic extent.

8. The method of claim 7 further comprising:

integrating the ablation instrument with a catheter configured for intravenous displacement along a blood vessel; and accessing the tissue region adjacent to the blood vessel.

9. The method of claim 7 further comprising:

integrating the ablation instrument with an elongated probe configured for insertion into neurological tissue; and accessing the tissue region via proximity of the elongated probe.

10. The method of claim 1 wherein the photonic signal is a laser signal having a wavelength based on a response of hemoglobin or myoglobin in the tissue.

11. A spectroscopic imaging device, comprising:

a light source for directing a photonic signal at a tissue treatment site;

one or more transducers disposed over the tissue treatment site and in a return path for receiving an acoustic signal indicative of a temperature induced response of the tissue resulting from the photonic signal;

a processor with photoacoustic logic for computing a necrotic extent indicative of a degree of necrosis of the tissue; and a rendering device for rendering a mapping of the computed necrotic extent by mapping the received acoustic signal to a visual rendering for quantifying the extent of ablation-induced necrosis with respect to a non-necrotic viable tissue:

the processor further configured to compute the necrotic extent based on a fraction of quantified ablated tissue contrast over a total contrast from both ablated and non-ablated tissues based on a ratio attributable to respective different wavelengths corresponding to the necrotic and non-necrotic tissue, and visualizing the computed necrotic extent as a continuous colormap to highlight the necrotic tissue and extent.

12. The device of claim 11, further comprising an interface to an ablation therapy device, the ablation therapy device operative for at least one of radiofrequency (RF) ablation, cryoablation, and pulsed-field ablation (PFA).

13. The device of claim 11, wherein the photoacoustic logic is configured to determine the necrotic extent based on a contrast of spectral decomposition between a necrotic tissue and the non-necrotic tissue in the received acoustic signal.

14. The device of claim 13 wherein the spectral decomposition is based on optical absorption characteristics between necrotic and non-necrotic tissue resulting from chromophores in the tissue.

15. The device of claim 13 wherein the spectral decomposition distinguishes a contribution of a contrast of the ablated tissue from that of the non-ablated tissue.

16. The device of claim 11 wherein mapping further comprises mapping the received acoustic signal to a visual rendering for quantifying the extent of ablation-induced necrosis with respect to the non-necrotic viable tissue.

17. A system for spectroscopic photoacoustic imaging of a tissue treatment region, comprising:

a light source for directing a photonic signal at a tissue treatment site;

one or more transducers disposed over the tissue treatment site and in a return path for receiving an acoustic signal indicative of a temperature induced response of the tissue resulting from the photonic signal;

a processor with photoacoustic logic for computing a necrotic extent indicative of a degree of necrosis of the tissue, the photoacoustic logic responsive to the acoustic signal for imaging the tissue treatment site for distinguishing necrotic and viable tissue by computing the necrotic extent based on a fraction of quantified ablated tissue contrast over a total contrast from both ablated and non-ablated tissues based on a ratio attributable to respective different wavelengths corresponding to the necrotic and non-necrotic tissue;

an output device for rendering a mapping for providing a necrotic extent indicative of a degree of necrosis for the imaged tissue in the tissue treatment site by mapping the received acoustic signal to a visual rendering for quantifying the extent of ablation-induced necrosis with respect to the viable tissue, and visualizing the computed necrotic extent as a continuous colormap to highlight the necrotic tissue and extent; and an ablation device configured for delivering ablation therapy to portions of the tissue region based on the rendered mapping.

18. The system of claim 17 wherein imaging further comprises directing a multiwavelength photoacoustic signal at the tissue region, the multiwavelength photoacoustic signal providing specific target contrasts based on spectral decomposition of the necrotic and viable tissue.

19. The method of claim 1 wherein quantifying the extent of ablation induced necrosis includes distinguishing between wavelengths corresponding to reversible tissue edema and irreversible lesions defining necrosis.

* * * * *